(12) United States Patent
Govari

(10) Patent No.: US 11,826,088 B2
(45) Date of Patent: Nov. 28, 2023

(54) ADJUSTING PHASES OF MULTIPHASE ABLATION GENERATOR TO DETECT CONTACT

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 623 days.

(21) Appl. No.: 16/709,802

(22) Filed: Dec. 10, 2019

(65) Prior Publication Data
US 2020/0205876 A1    Jul. 2, 2020

Related U.S. Application Data

(60) Provisional application No. 62/786,037, filed on Dec. 28, 2018.

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1492* (2013.01); *A61B 2017/00199* (2013.01);
(Continued)

(58) Field of Classification Search
CPC .. A61B 2018/0075; A61B 2018/00791; A61B 2018/00797; A61B 2018/00815;
(Continued)

(56) References Cited

U.S. PATENT DOCUMENTS 6,139,546 A    10/2000   Koenig et al.
6,226,542 B1    5/2001   Reisfeld
(Continued)

FOREIGN PATENT DOCUMENTS

JP    2002513617 A    5/2002
JP    2014500058 A    1/2014
(Continued)

OTHER PUBLICATIONS

European Search Report issued in European Patent Application No. 19 21 9611 dated Jun. 18, 2020.
(Continued)

*Primary Examiner* — Linda C Dvorak
*Assistant Examiner* — Nicholas S Borsch
(74) *Attorney, Agent, or Firm* — Troutman Pepper Hamilton Sanders LLP

(57) ABSTRACT

A radio frequency ablation system, includes a single frequency RF signal generator, control circuitry configured to set phases and amplitudes of a plurality of replicas of the RF signal, a plurality of non-linear amplifiers, configured to amplify the plurality of replicas of the RF signal, and to drive a respective plurality of ablation electrodes in a patient body with the amplified replicas. A processor is configured to receive a superposition of the plurality of replicas as a return signal from a body surface patch electrode, and to adaptively adjust phases and amplitudes of the amplified replicas in response to the return signal with the control circuitry to zero crosstalk currents. In a tissue contact check mode of operation the phases of the amplified replicas are identical, and in an ablation mode of operation the phases of the amplified replicas differ from one another.

20 Claims, 9 Drawing Sheets

(51) Int. Cl.
*A61B 18/00* (2006.01)
*A61B 18/16* (2006.01)
*A61B 34/20* (2016.01)
*A61B 17/00* (2006.01)

(52) U.S. Cl.
CPC .............. *A61B 2018/00351* (2013.01); *A61B 2018/00577* (2013.01); *A61B 2018/00827* (2013.01); *A61B 2018/00869* (2013.01); *A61B 2018/00875* (2013.01); *A61B 2018/00892* (2013.01); *A61B 2018/1467* (2013.01); *A61B 2018/167* (2013.01); *A61B 2034/2051* (2016.02)

(58) Field of Classification Search
CPC ........... A61B 2018/00821; A61B 2018/00875; A61B 18/1206; A61B 18/1492; A61B 2017/00199; A61B 2018/00351; A61B 2018/00577; A61B 2018/00827; A61B 2018/00869; A61B 2018/00892; A61B 2018/1467; A61B 2018/167; A61B 2034/2051; A61B 18/1233; A61B 2018/00642; A61B 2018/00654; A61B 2018/00708; A61B 2018/1293; A61B 2090/065; A61B 18/12; A61B 2018/126
USPC ......................................... 606/32, 33, 34, 41
See application file for complete search history.

(56) References Cited

U.S. PATENT DOCUMENTS

| | | | |
|---|---|---|---|
| 6,301,496 B1 | 10/2001 | Reisfeld | |
| 6,589,237 B2 * | 7/2003 | Woloszko | A61B 18/1485 604/35 |
| 6,814,733 B2 | 11/2004 | Schwartz et al. | |
| 6,892,091 B1 | 5/2005 | Ben-Haim et al. | |
| 6,997,924 B2 | 2/2006 | Schwartz et al. | |
| 7,156,816 B2 | 1/2007 | Schwartz et al. | |
| 7,536,218 B2 | 5/2009 | Govari et al. | |
| 7,756,576 B2 | 7/2010 | Levin | |
| 7,775,576 B2 | 8/2010 | Der Marderosian et al. | |
| 7,848,787 B2 | 12/2010 | Osadchy | |
| 7,869,865 B2 | 1/2011 | Govari et al. | |
| 8,456,182 B2 | 6/2013 | Bar-Tal et al. | |
| 8,478,383 B2 | 7/2013 | Bar-Tal et al. | |
| 9,168,004 B2 | 10/2015 | Gliner et al. | |
| 10,945,781 B2 | 3/2021 | Govari | |
| 11,304,603 B2 | 4/2022 | Gliner | |
| 2001/0008967 A1 * | 7/2001 | Sherman | A61B 18/1492 606/41 |
| 2006/0173251 A1 | 8/2006 | Govari et al. | |
| 2007/0038078 A1 | 2/2007 | Osadchy | |
| 2008/0312713 A1 * | 12/2008 | Wilfley | A61B 18/1492 606/41 |
| 2010/0030210 A1 * | 2/2010 | Paulus | A61B 18/1206 606/38 |
| 2013/0006238 A1 * | 1/2013 | Ditter | A61B 18/1492 606/41 |
| 2014/0058248 A1 * | 2/2014 | Leussler | A61B 18/18 600/411 |
| 2015/0272655 A1 | 10/2015 | Condie et al. | |

FOREIGN PATENT DOCUMENTS

| | | |
|---|---|---|
| JP | 2016185295 A | 10/2016 |
| WO | 99/56644 A1 | 11/1999 |
| WO | 2007/067628 A1 | 6/2007 |
| WO | 2008/157399 A1 | 12/2008 |
| WO | 2016/160448 A2 | 10/2016 |
| WO | 2018/200865 A1 | 11/2018 |

OTHER PUBLICATIONS

Deno, D. C., et al. "Measurement of Electrical Coupling Between Cardiac Ablation Catheters and Tissue" IEEE Transactions on Biomedical Engineering 61(3):765-774 (Mar. 2014) cited in Specification.

Borganelli, M., et al. "Determinants of Impedance During Radiofrequency Catheter Ablation in Humans" Department of Internal Medicine, Division of Cardiology, University of Michigan Medical Center, 1500 E. Medical Center Drive, BI F245, Ann Arbor, Michigan 48109-0022, Dec. 1991, pp. 1095-1097 cited in Specification.

Berjano, E. J., "Theoretical modeling for radiofrequency ablation: state of-the-art and challenges for the future" BioMedical Engineering OnLine, pp. 1-17 (Apr. 18, 2006) cited in Specification.

Notice of Reasons for Refusal dated Jul. 11, 2023, from corresponding Japanese Application No. 2019-237803.

* cited by examiner

ADJUSTING PHASES OF MULTIPHASE ABLATION GENERATOR TO DETECT CONTACT

PRIORITY CLAIM

This application claims the benefit of U.S. Provisional Patent Application 62/786,037 filed Dec. 28, 2018, which prior application is hereby incorporated by reference as if set forth in full herein.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to performing internal medical examinations on the body. More particularly, this invention relates to catheters adapted for transferring non-mechanical forms of energy to or from the body for diagnosis and therapy.

2. Description of the Related Art

The meanings of certain acronyms and abbreviations used herein are given in Table 1.

TABLE 1

| Acronyms and Abbreviations | |
|---|---|
| RF | Radiofrequency |
| ACL | Active Current Location |

Various known invasive medical instrument designs apply ablative radiofrequency (RF) energy to a patient's tissue using multiple electrodes. For example, U.S. Patent Application Publication 2015/0272655 describes a system and method for preventing unintended tissue damage from the delivery of unintended bipolar RF energy. The system may include a multi-electrode ablation device and an RF delivery unit. The RF delivery unit may transmit unipolar energy to the plurality of electrodes, the energy being in phase, with all electrodes delivering the same voltage and being activated at the same time to deliver no bipolar energy. Additionally or alternatively, the RF delivery unit may transmit bipolar energy to the electrodes. Here, voltage differences between each pair of adjacent electrodes may be monitored and the level of bipolar energy being delivered may be calculated. The voltage of energy delivered to at least one electrode in each adjacent electrode pair may be adjusted if the amount of delivered bipolar energy exceeds a safety threshold.

The advanced current location (ACL) system finds the location of an electrode in a patient's body by measuring alternating currents from the electrode to back patches on the patient's skin. At present, for catheters with multiple electrodes, the currents injected into the electrodes are differentiated and separately analyzed by modulating the alternating current injected into the electrodes with a frequency, which is selected to be unique for a given electrode. However, the different alternating currents are generated by class A amplifiers, and these are very inefficient. Documents describing the ACL system is shown and described in U.S. Pat. No. 7,536,218; 7,775,576; 7,848,787; 7,869,865; or 8,456,182, all of which are hereby incorporated by reference into this application.

SUMMARY OF THE INVENTION

According to disclosed embodiments of the invention, a multi-electrode ablation catheter has two modes of operation. In a tissue contact check mode of operation to ascertain contact between the ablation electrodes and the target tissue, the currents in the electrodes all have the same phase and a common frequency $\omega$. In an ablation mode the electrode currents are modulated at the common frequency $\omega$, but the phases of the currents flowing through the electrodes are individually varied in order to minimize crosstalk currents.

There is provided according to embodiments of the invention a radio frequency (RF) ablation system, which includes a signal generator configured to generate an RF signal at a given frequency, control circuitry configured to set phases and amplitudes of a plurality of replicas of the RF signal, a plurality of non-linear amplifiers, configured to amplify the plurality of replicas of the RF signal, and to drive a respective plurality of ablation electrodes in a patient body with the amplified replicas, and a processor. The processor is configured to receive a superposition of the plurality of replicas as a return signal, which is sensed by a patch electrode attached to the patient body, and to adaptively adjust phases and amplitudes of the amplified replicas in response to the return signal by controlling the control circuitry. In a tissue contact check mode of operation the phases of the amplified replicas are identical, and in an ablation mode of operation the phases of the amplified replicas differ from one another.

In the ablation mode of operation the phases of the amplified replicas differ from one another by at least 3.6 degrees.

According to an aspect of the system, the amplifiers comprise class-D amplifiers.

Yet another aspect of the system includes a measurement circuit, configured to measure the replicas that are amplified respectively by the amplifiers, wherein the processor is configured to adjust the phases and the amplitudes of the replicas based on the measured replicas in the ablation mode of operation.

There is further provided according to embodiments of the invention a method of ablation, which is carried out by generating a plurality of replicas of an RF signal at a given frequency, setting phases and amplitudes of the plurality of replicas, amplifying the plurality of replicas of the RF signal, and driving a respective plurality of ablation electrodes in a patient body with the amplified replicas. The method is further carried out by attaching a patch electrode to the patient body, receiving a superposition of the plurality of replicas as a return signal sensed by the patch electrode, adaptively adjusting phases and amplitudes of the amplified replicas in response to the return signal. The method is further carried out in a tissue contact check mode of operation, wherein the phases of the amplified replicas are identical, determining from the return signal that a state of contact exists between the ablation electrodes and target tissue in the patient body, and in an ablation mode of operation, wherein the phases of the amplified replicas differ from one another, ablating the target tissue with the ablation electrodes.

According to another aspect of the method, in the ablation mode of operation the phases of the amplified replicas differ from one another by at least 3.6 degrees.

According to an additional aspect of the method, amplifying is performed by class-D amplification.

According to still another aspect of the method, further making measurements of the replicas, and responsively to the measurements zeroing crosstalk currents between the ablation electrodes by adjusting the phases and the amplitudes of the replicas in the ablation mode of operation.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE MODES OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment. Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview

Figure 1:
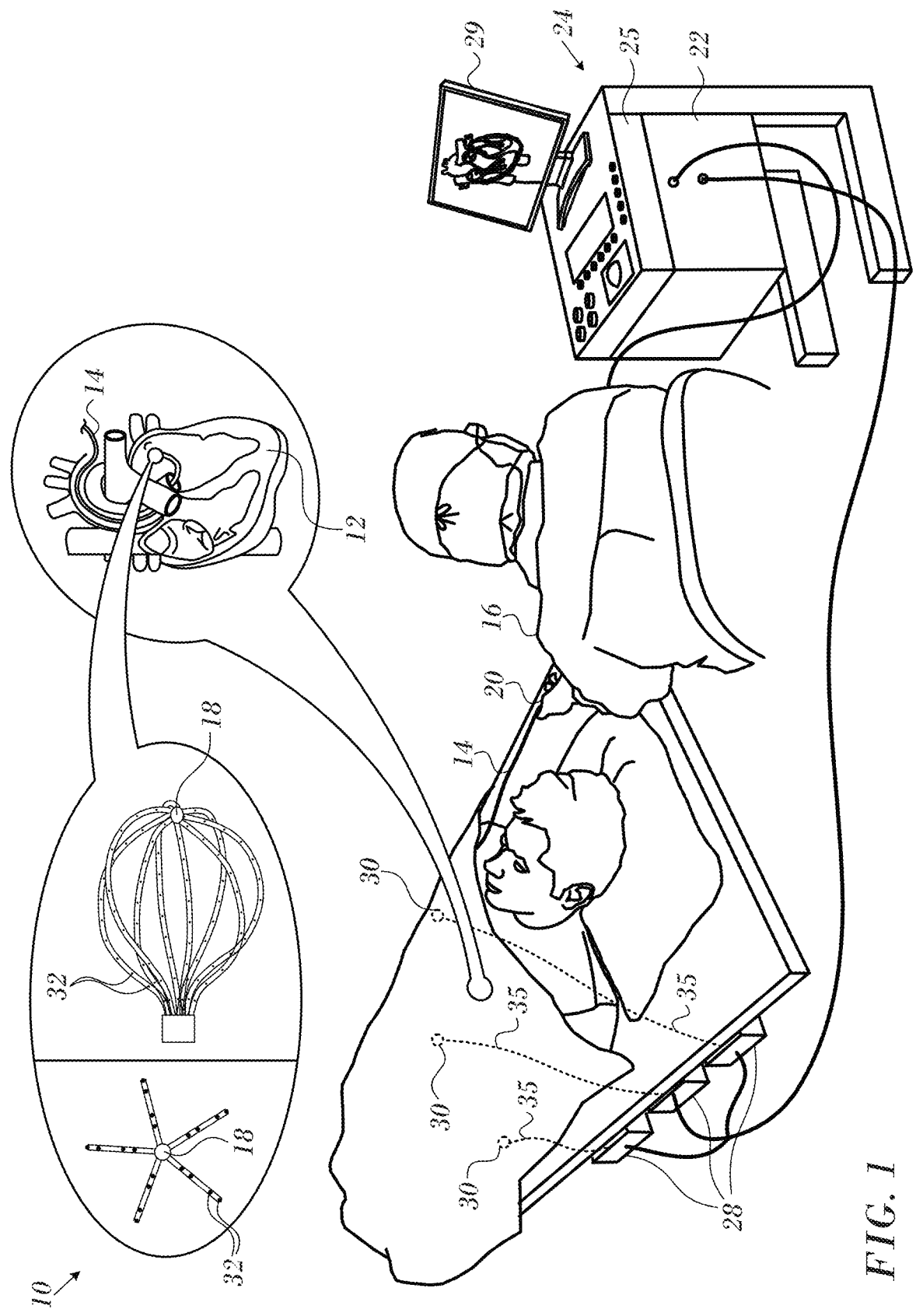
FIG. 1 is a pictorial illustration of a system in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference as if set forth in full herein.

The system 10 may comprise a general purpose or embedded computer processor, which is programmed with suitable software for carrying out the functions described hereinbelow. Thus, although portions of the system 10 shown in other drawing figures herein are shown as comprising several separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 33 Technology Drive, Irvine, CA 92618. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a balloon or basket catheter, or a spine catheter as shown in FIG. 1. In any case there are multiple electrodes 32, which are used as sensing electrodes and have known locations on the basket or spine and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference as if set forth in full herein.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with active current location (ACL) patches 30 and other components of a positioning sub-system for measuring location and orientation coordinates of the catheter 14. The processor 22, or another processor (not shown) may be an element of the positioning subsystem. The electrodes 32 and the body surface patches 30 may be used to measure tissue impedance at the ablation site as taught in U.S. Pat. No. 7,536,218, issued to Govari et al., which is herein incorporated by reference as if set forth in full herein. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference as if set forth in full herein.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference as if set forth in full herein, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images. Electrical coupling is described in "Measurement of Electrical Coupling Between Cardiac Ablation Catheters and Tissue" by D. Curtis Deno*, Member, IEEE, Haris J. Sih, Stephan P. Miller, Liane R. Teplitsky, and Russ Kuenzi, IEEE TRANSACTIONS ON BIOMEDICAL ENGINEERING, VOL. 61, NO. 3, March 2014; impedance ranges in humans is described in "Determinants of impedance During Radiofrequency Catheter Ablation in Humans" by Mark Borganelli, MD, Rafel El-Atassi, MD, Angel Leon, MD, Steven J. Kalbfleisch, MD, Hugh Calkins, MD, Fred Morady, MD, and Jonathan J. Langberg, MD; Department of Internal Medicine, Division of Cardiology, University of Michigan Medical Center, 1500 E. Medical Center Drive, Bl F245, Ann Arbor, Michigan 48109-0022, December 1991; Modeling of impedance controlled ablation is described in "Theoretical modeling for radiofrequency ablation: state-of-the-art and challenges for the future" Enrique J Berjano, 18 Apr. 2006 BioMedical Engineering OnLine2006, all of which are incorporated by reference as if set forth in full herein.

ACL System

The ACL system is one embodiment in which the principles of the invention may be applied. A brief description of the ACL system is presented herein for convenience. Further details are found in commonly assigned application Ser. No. 15/681,474, titled as "Advanced Current Location (ACL) Automatic Map Rotation to Detect Holes in Current Position Map (CPM) Mapping" filed on Aug. 21, 2017, which is herein incorporated by reference as if set forth in full herein.

Figure 2:
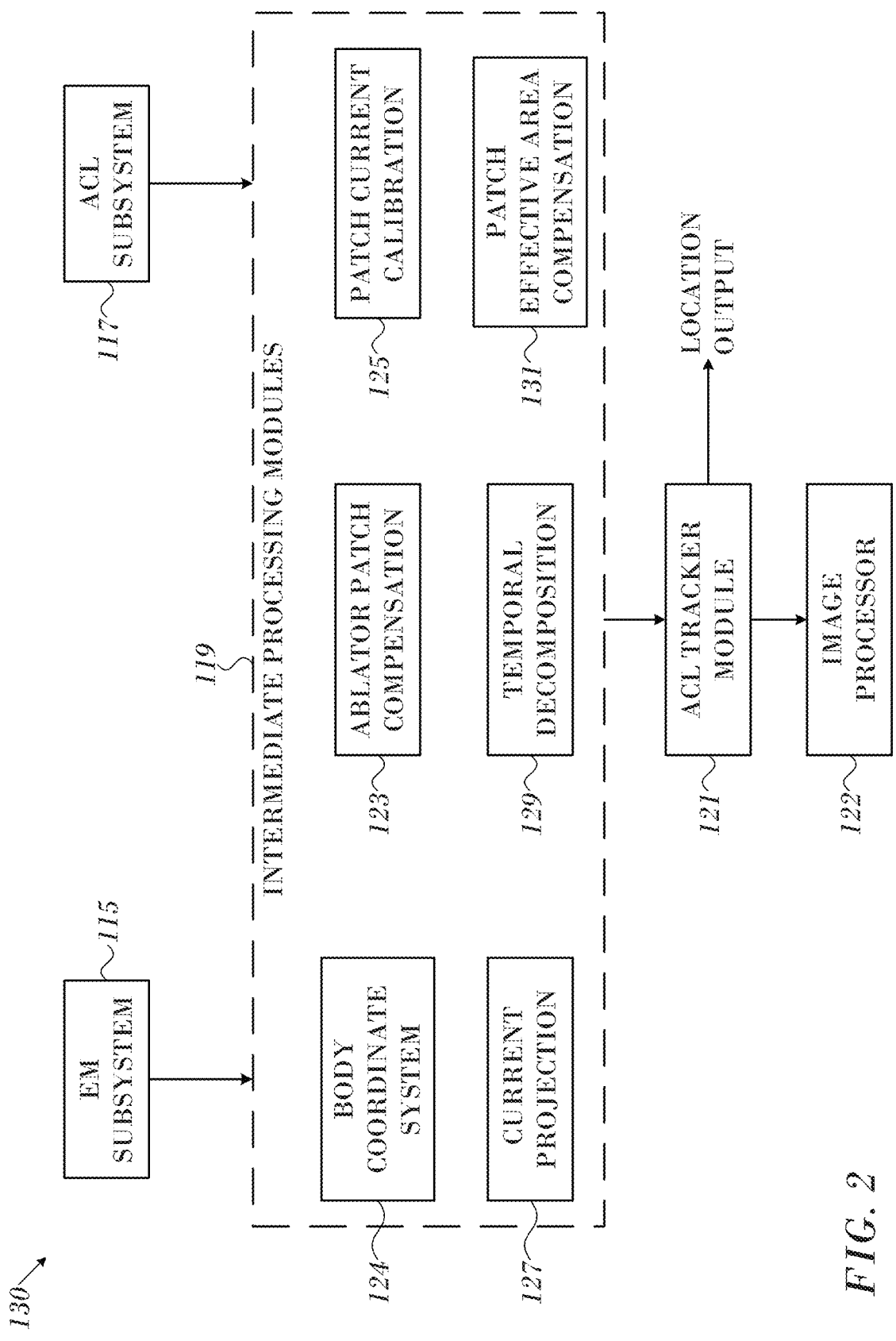
FIG. 2 is a block diagram of an ACL system in accordance with an embodiment of the invention.

Reference is now made to FIG. 2, which is a block diagram of an ACL system 130 according to an embodiment of the present invention. To operate the system 130 an operator first operates the system in a calibration phase after which the system is operated in a tracking phase. Details of the actions performed in the two phases are described in the above-noted application Ser. No. 15/681,474.

Figure 3:
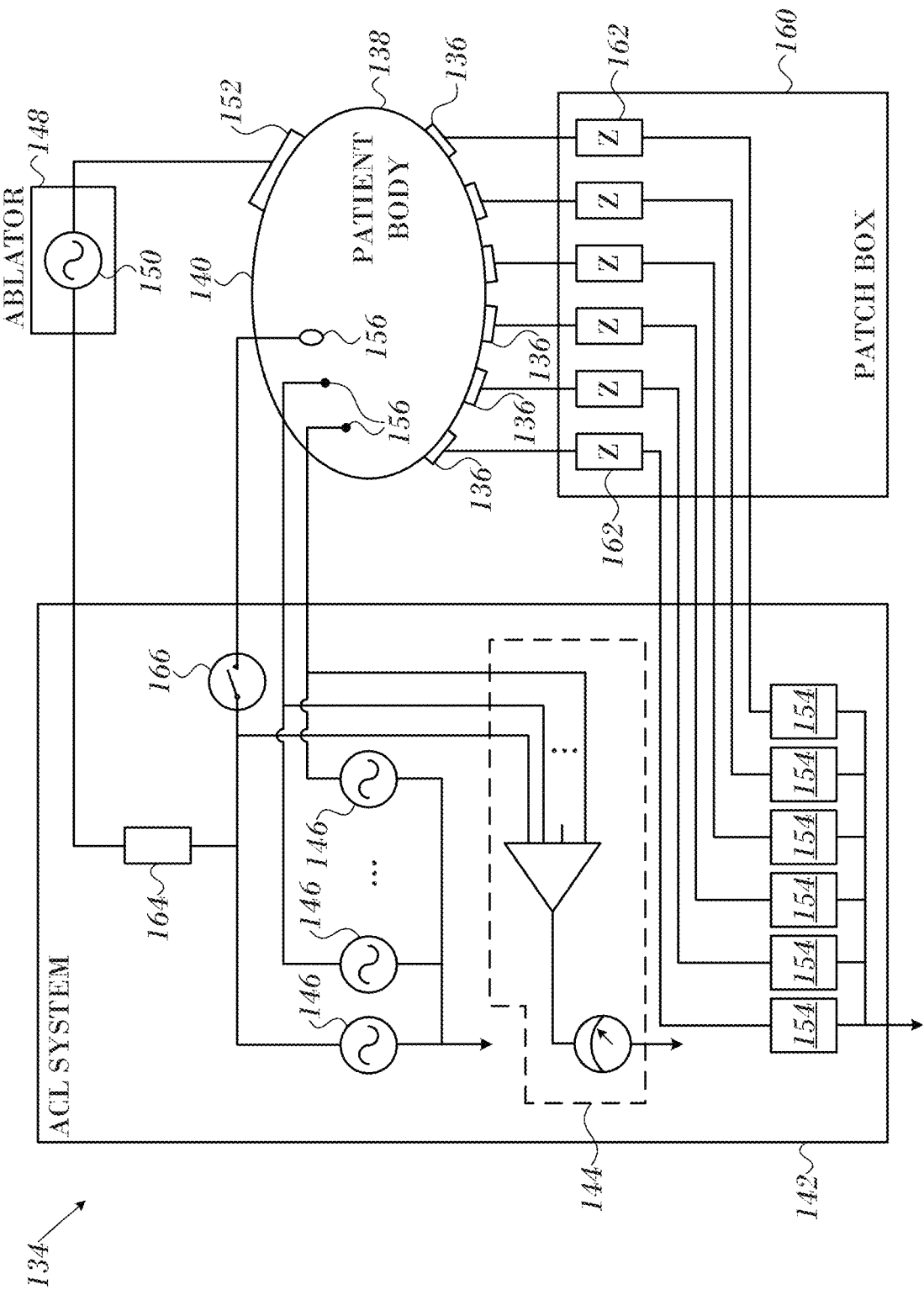
FIG. 3 is a schematic diagram of an ACL circuit in accordance with an embodiment of the invention.

Reference is now made to FIG. 3, which is a schematic diagram of an ablation and active current location (ACL) circuit 134 for use with the system shown in FIG. 1. This arrangement is similar to that described in U.S. Patent Application Publications 2006/0173251, to Govari et al., and 2007/0038078, to Osadchy, which are herein incorporated by reference as if set forth in full herein. The arrangement can be modified to operate in accordance with the principles of the present invention. A brief description follows for convenience of presentation.

A plurality of body surface electrodes 136, which can be adhesive skin patches, are coupled to a body surface 138 (e.g., the skin) of subject 140. The body surface electrodes 136 are sometimes referred to herein as "patches". In cardiac applications the body surface electrodes 136 are usually distributed so as to surround the heart, three on the chest of the subject and three on the back. However, the number of the body surface electrodes 136 is not critical, and they may be placed at convenient locations on the body surface 138 in the general vicinity of the site of the medical procedure.

Figure 4:
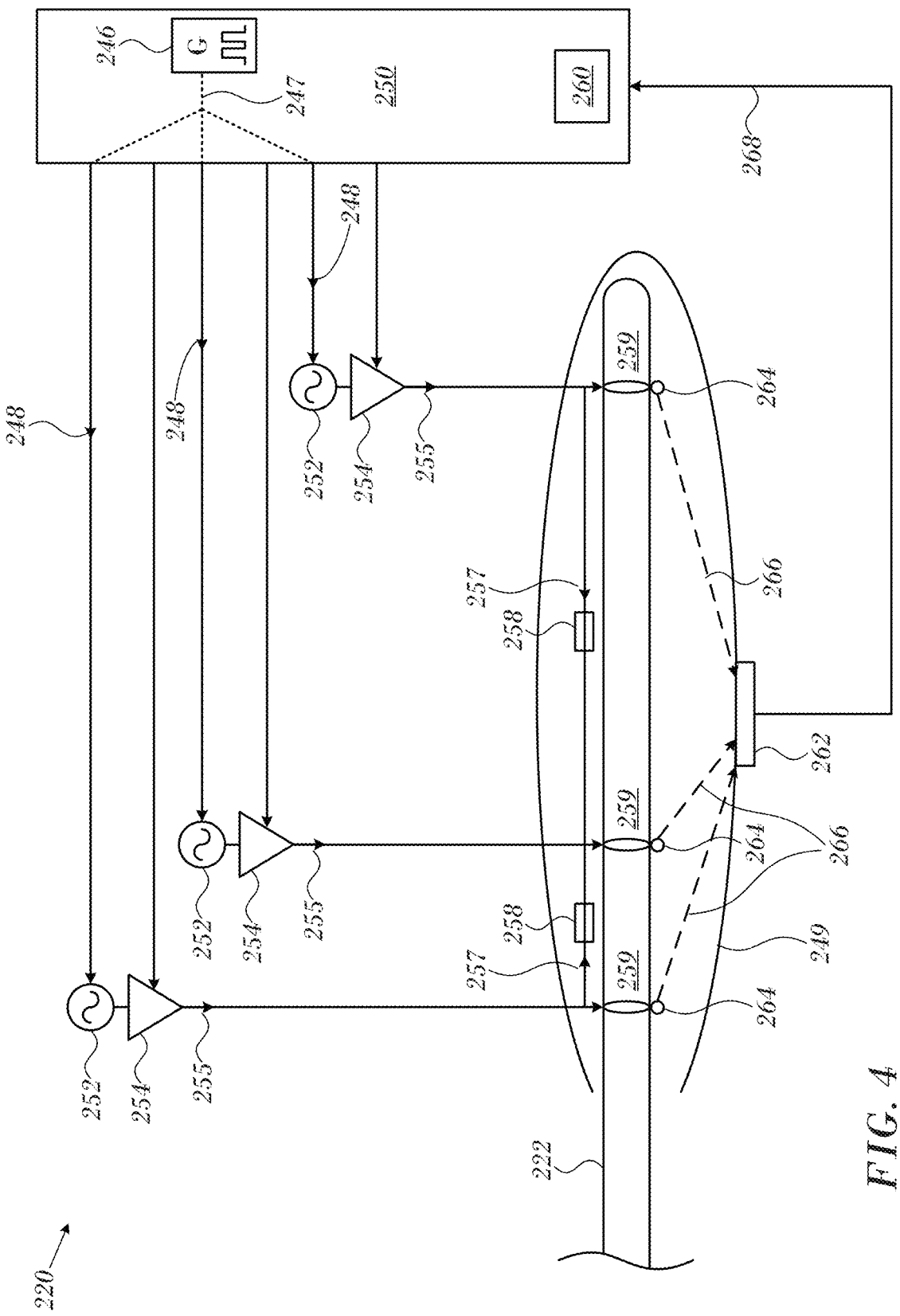
FIG. 4 is a schematic diagram of catheter-based ablation system using Class-D amplifiers in accordance with an embodiment of the invention.

A control unit 142, normally disposed in the console 24 (FIG. 1), includes current measurement circuitry 144 and one or more catheter electrode transmitters 146 for driving a current through one or more of the electrodes 136 to one or more of the body surface electrodes 136 at a single frequency, as is explained below. The control unit 142 is linked to a positioning processor. The control unit 142 is linked to an ablator 148, which comprises at least one ablation generator 150. Currents through the body surface electrodes 136 and an ablator body surface electrode 152 flow in a circuit with the ablation generator 150 and are measured by respective current measurement circuits that are disposed within body electrode receivers 154, sometimes referred to herein as "patch measurement circuits". The body electrode receivers 154 are typically incorporated in the control unit 142. Alternatively, they may be affixed to the body surface electrodes 136. Catheter electrodes are represented in FIG. 4 as measurement electrodes 156 (circles) and a dual-purpose electrode 158 (ellipse). The dual-purpose electrode 158 functions as an ablation electrode and also serves as one of the measurement electrodes.

The body surface electrodes 136 are connected to the body electrode receivers 154 via a patch box 160, which protects the system from ablation and defibrillation currents. Typically, the system is configured with six body electrode receivers 154. The patch box parasitic impedances 162 (Z), are measured during production and thus known a priori. These impedances are discussed below.

Typically, although only two measurement electrodes 156 are shown for convenience, about 80 measurement electrodes are used for impedance measurements. Typically, there are one or two ablation electrodes. The coordinates of a catheter inside the body are determined in the positioning system by passing currents between electrodes on the catheter and the body surface electrodes 136.

The control unit 142 may also control an ablation circuit, comprising ablator 148, and the dual-purpose electrode 158. The ablator 148 is typically disposed externally to the control unit 142 and incorporates the ablation generator 150. It connects with the ablator body surface electrode 152 and to an ablator filter 164, which in this example is shown within the control unit 142. However, this location is not essential. A switch 166 configures the ablator circuit for different modes of operation as described below. Voltage measurement circuitry is provided for determining the output of the catheter electrode transmitters 146. It will be noted from inspection of FIG. 4 that the ablation circuit is connected to one of the catheter electrode transmitters 146.

Single Frequency Generator for Multiple.Ablation Electrodes

FIG. 4 is a schematic diagram of catheter-based ablation system 220 using Class-D amplifiers 254 in accordance with an embodiment of the invention. Physically, as illustrated, distal end 222 of a catheter is fitted with an RF ablation device comprising a plurality of electrodes 259, wherein the outputs of amplifiers 254 are each coupled to electrodes 259 by wiring passing through the catheter, which is coupled at its proximal end to control console comprising control unit 250.

The distal end of the catheter is shown as a linear array of electrodes only for clarity. In practice, the distal end typically comprises a multi-electrode geometry suitable for the ablation procedure in question. Example configurations are an inflatable-balloon or an expandable-basket assembly, used for performing ablation of pulmonary veins.

In the present example, control unit 250 controls in parallel a number of Class-D amplifiers that is equal to the number of electrodes 259. Each of the Class-D amplifiers comprises a phase shifter 252 and amplifier 254. Control unit 250 comprises a common signal generator 246 that generates a common RF signal 247, split into replicated signals (or "replicas") 248 of the RF signal 247 for driving amplifiers 254. Control unit 250 commands separately each of phase shifters 252 to assign a respective phase to an input current waveform of amplifier 254, which is then amplified to become output current 255 injected into a patient's body 249 through the associated electrode 259.

As seen in the figure, resulting ablation currents 266 flow locally through the ablated tissue 264 and then through the patient body 249 and are collected by a common back patch electrode 262. However, the finite resistance of tissue between any two electrodes, for example through blood in the case of ablation of blood vessels, as illustrated by coupling resistances 258, can cause part of the injected current 255 to take a path from one electrode to another in the form of crosstalk currents 257.

Control unit 250 comprises an analyzer 260, which analyzes a return current 268, and based on its measured instantaneous amplitude and phase, possibly among other inputs required for the calculation, determines the actual current amplitudes of each of the injected ablation currents 266. Based on requirements and calculation steps implemented in an optimization algorithm, the analyzer adjusts the amplitudes or phases or both of one or more of currents 255 to optimize the amplitudes and phases or both of the currents 255 according to certain requirements, some of which are detailed below. Control unit 250 receives the optimized amplitudes and phases in realtime and instructs phase shifter 252 or amplifiers 254 or both in realtime to responsively modify at least part of the injected phases and amplitudes of currents 255. In one implementation, the optimization algorithm may utilize the instantaneously measured output voltages and currents of amplifiers 254 for adjusting crosstalk currents 257 in realtime. For example, the algorithm may diagonalize a 'current matrix', as to zero the crosstalk currents 257. Additionally or alternatively, other optimization algorithms may be applied, utilizing given constraints and/or cost functions, such as those incorporating the measured instantaneous amplitude and phase of back patch electrode 262.

Figure 5:
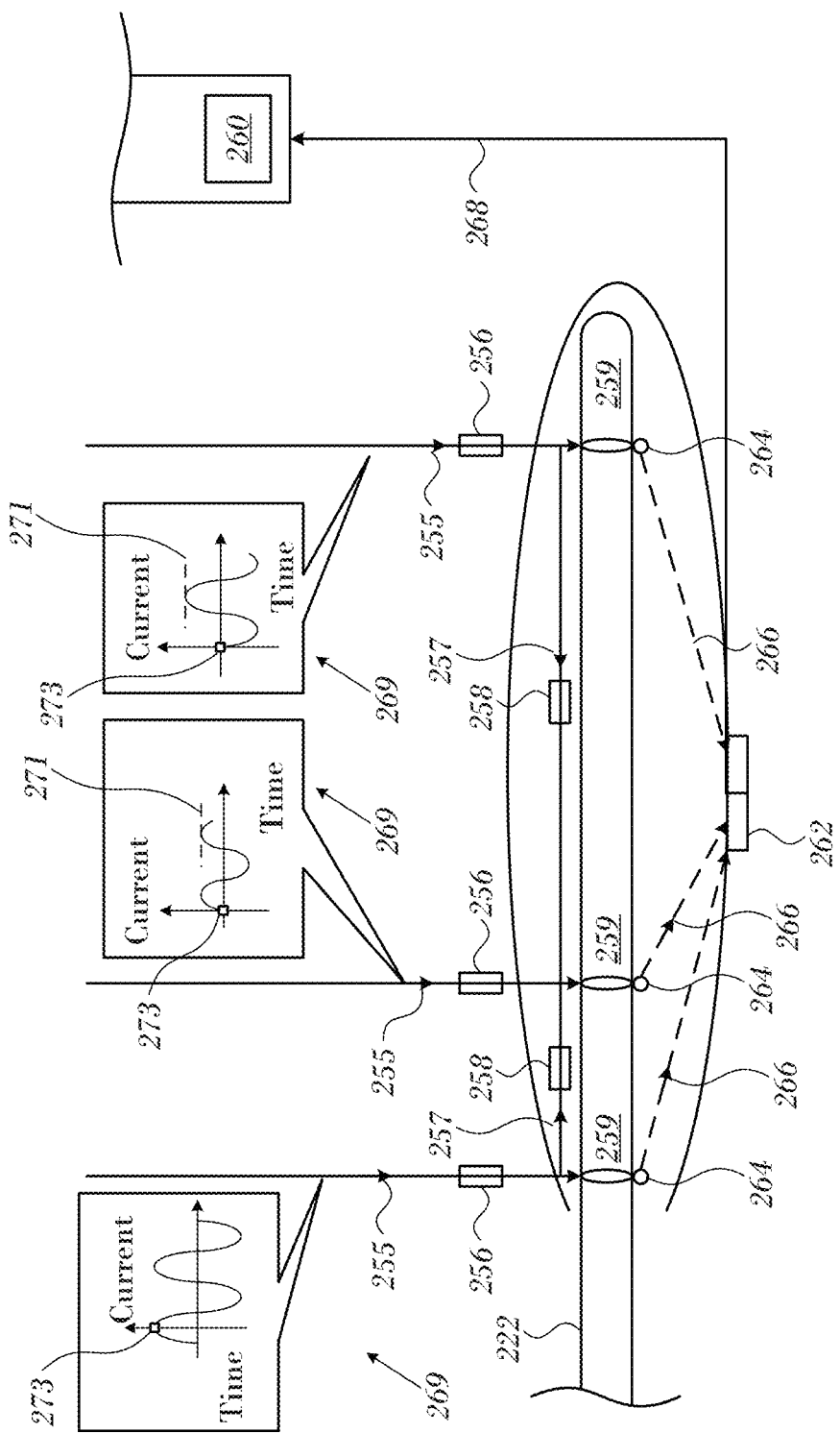
FIG. 5 is a schematic diagram showing certain details of the operation of the system shown in FIG. 4 in accordance with an embodiment of the invention.

FIG. 5 is a schematic diagram showing certain details of the operation of the system 220 in accordance with an embodiment of the invention. As seen in the figure, the waveforms in insets 269 comprise in general different values of amplitudes 271 and phases 273. Voltage and current sensors 256 measure the amplifiers output voltage and currents, and analyzer 260 measures the instantaneous amplitude and phase of the return current 268 and uses this information, among others, for extracting the actual electrode output voltage and currents. The arrangement in FIG. 5 thus isolates and measures the various current amplitudes in currents 255, 266 of each and one of electrodes 259 and deduces the crosstalk currents 257.

Crosstalk currents 257 can be reduced and even canceled by forcing similar, or practically identical, voltages on part or all of the electrodes 259 in realtime during the ablation process. This setting is achieved by modulating the currents of all electrodes with the same frequency ω, and by selecting in real-time the individual amplitudes and phases of currents 255, as seen in insets 269. Thus, when the voltage differences between any two electrodes (namely, over resistances 258) are kept minimal at all times, the cross-talk currents between any two electrodes are reduced and even canceled altogether in certain cases.

As noted above, to practically achieve such a minimization of constantly varying crosstalk currents, or even their cancellation, the return current 268 should be analyzed by analyzer 260 at sufficiently high rate such that amplitude and phase selection occur at a sufficiently high rate and with short enough response times. This closed-loop fit of analysis modification of the currents can be achieved by using proper electronic circuits and non-linear amplifiers, such as phase-shifters and Class-D amplifiers operating, for example, at a frequency range in the kHZ to MHz spectrum.

Further details regarding the configuration and operation of the system 220 are disclosed in commonly assigned copending application Ser. No. 15/697,811, entitled Variable Phase Generation And Detection For Radio-Frequency (RF) Ablation, filed on Sep. 7, 2017, which is herein incorporated by reference as if set forth in full herein.

Phase Adjustment

In order for ablation to be effective the electrodes 259 (FIG. 4) must be in contact with the body tissue being ablated. One way of detecting contact is by observing a change in the impedance on contact, using the circuitry described in FIG. 2 and FIG. 3. However, the change in impedance for any given electrode is small, although the sensitivity can be improved using the methods described in commonly assigned U.S. Pat. No. 9,168,004 to Govari et al., entitled Machine Learning in Determining Catheter Electrode Contact, which is herein incorporated by reference as if set forth in full herein.

Figure 6:
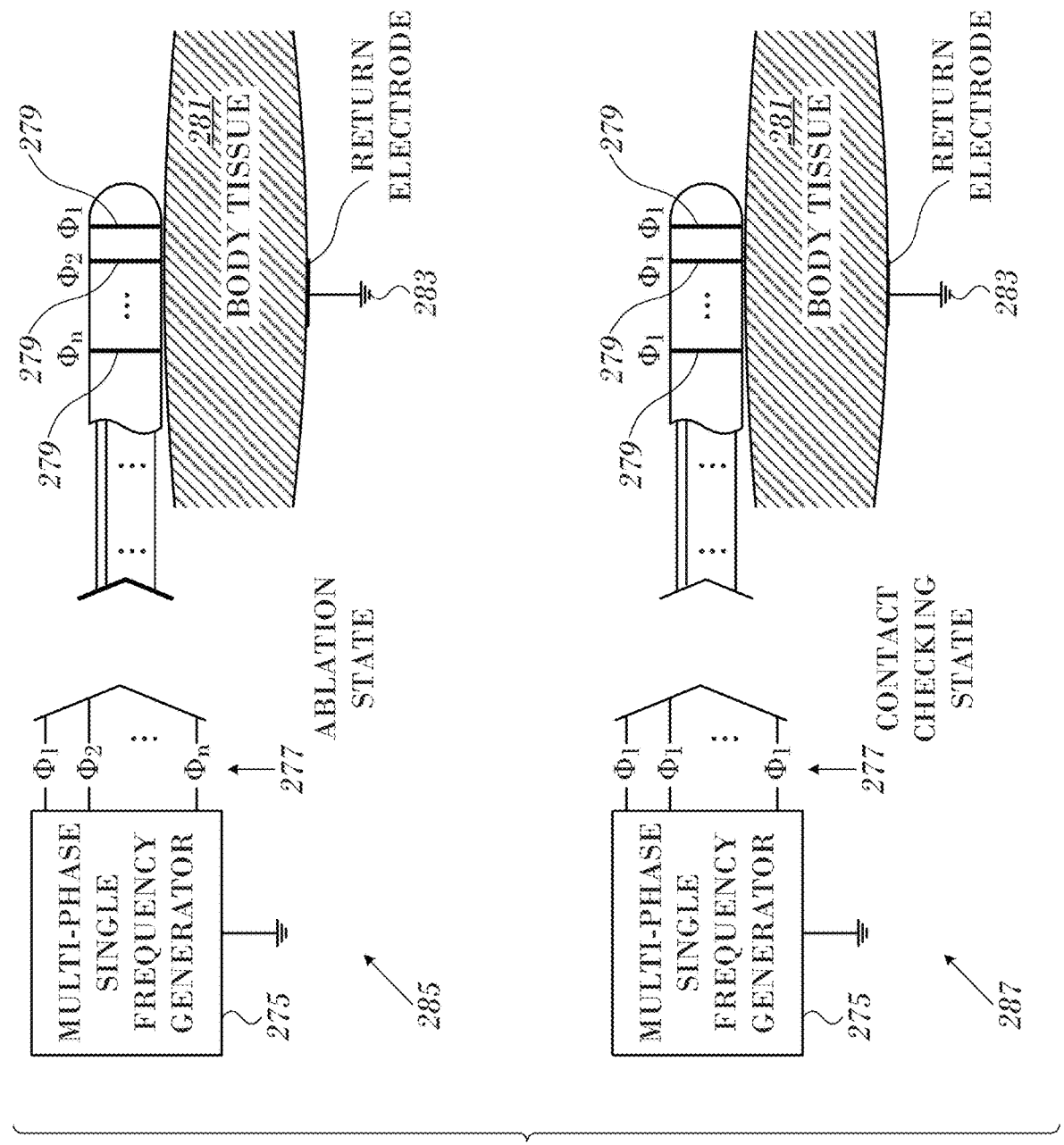
FIG. 6 is a set of schematics that illustrate two modes of operation of the system shown in FIG. 4 in accordance with an embodiment of the invention.

The inventors have devised a technique to reliably determine electrode contact with the ablation site via a tissue contact check mode of operation, in which the phases of the electrode currents at the common frequency ω are generally identical. FIG. 6 is a set of schematics that illustrate two modes of operation of the exemplary system 220 (FIG. 4). A multiphase single frequency generator 275 produces output currents 277 that flow through respective catheter electrodes 279 and thence through body tissue 281 and return electrode 283. In an ablation mode of operation, as shown in diagram 285 in the upper part of FIG. 6, the output currents 277 and the currents in the electrodes 279 have different phases $\Phi_1$-$\Phi_n$. The phase difference between any two electrodes should be at least 1/100 of the period, e.g., approximately 3.6°.

Diagram 287 in the lower part of the figure illustrates a tissue contact check mode of operation. The output currents 277 and the currents in the electrodes 279 produced by the single frequency generator 275 all have the same phase $\Phi_1$. When the supply to each electrode has a different phase, the generator 275 can operate at a relatively low voltage. Depending on the impedance of the body, the voltage for ablation can be from approximately 27V RMS (for tissue impedance of approximately 50 ohms) to 39V RMS (for tissue impedance of approximately 100 ohms) and to 47V RMS (where tissue impedance is approximately 150 ohms). However, for tissue contact checking, a large voltage is needed in order to overcome the body tissue impedance. Hence, the tissue contact check mode of operation is impractical for ablation.

Figure 7:
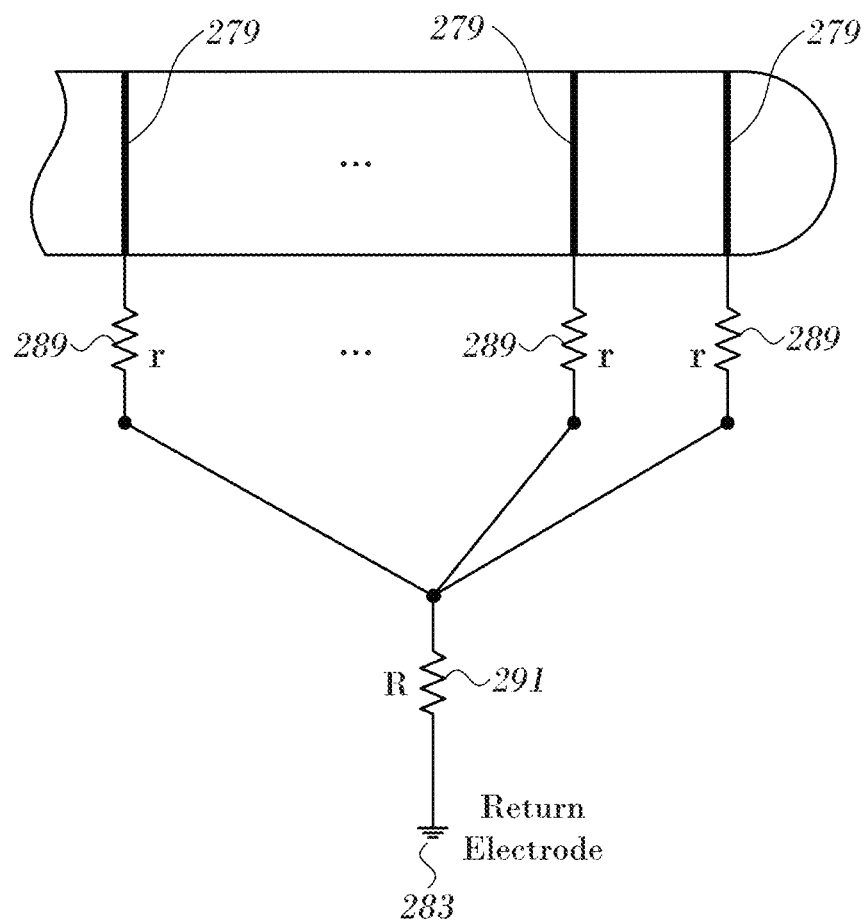
FIG. 7 schematically illustrates resistances present in the system configured for a mode of operation shown in FIG. 6.

Nevertheless, the inventors have devised a technique to exploit this behavior of the body impedance to allow for the same electrodes used in ablating to determine sufficient tissue contact during the same ablation procedure. Specifically, FIG. 7 schematically illustrates resistances present in the system configured according to the diagram 287 (FIG. 5). Each of n electrodes 279 sees a resistance 289 ($r$), and there is a single common resistance 291 (R) at the return electrode 283. If, assuming for simplicity that a current I flows through each of the n electrodes 279, then, since the currents are in phase, the current through common resistance 291 R is nI. Thus, the voltage seen by the generator for any electrode 279 is:

$$V=Ir+nIR.$$

The voltage V is effectively approximately a factor of n higher than the out-of-phase case and is the reason a common phase state should not be used for ablation. But the relatively large voltage in the tissue contact check configuration means that the small change in impedance that occurs on tissue contact effectively amplifies a change in the measured voltage, and so the tissue contact check configuration shown in FIG. 6 is a good way of measuring contact between target tissue and the ablation electrodes 279.

By virtue of the disclosure provided herein, we have devised the following method of ablating tissue that are in sufficient contact with an n number of ablation electrodes. The method can be achieved by reference to the ablation algorithm 300 illustrated in FIG. 8 which can be utilized by one skilled in the art to generate suitable software codes in a suitable computing platform for use in its intended purpose of ablating tissue that is in contact with the ablating electrode(s). It should be noted that algorithm 300 can be one of many algorithms devised for system 134, and for brevity, any other algorithms that are auxiliary to algorithm 300 will not be described.

Figure 8:
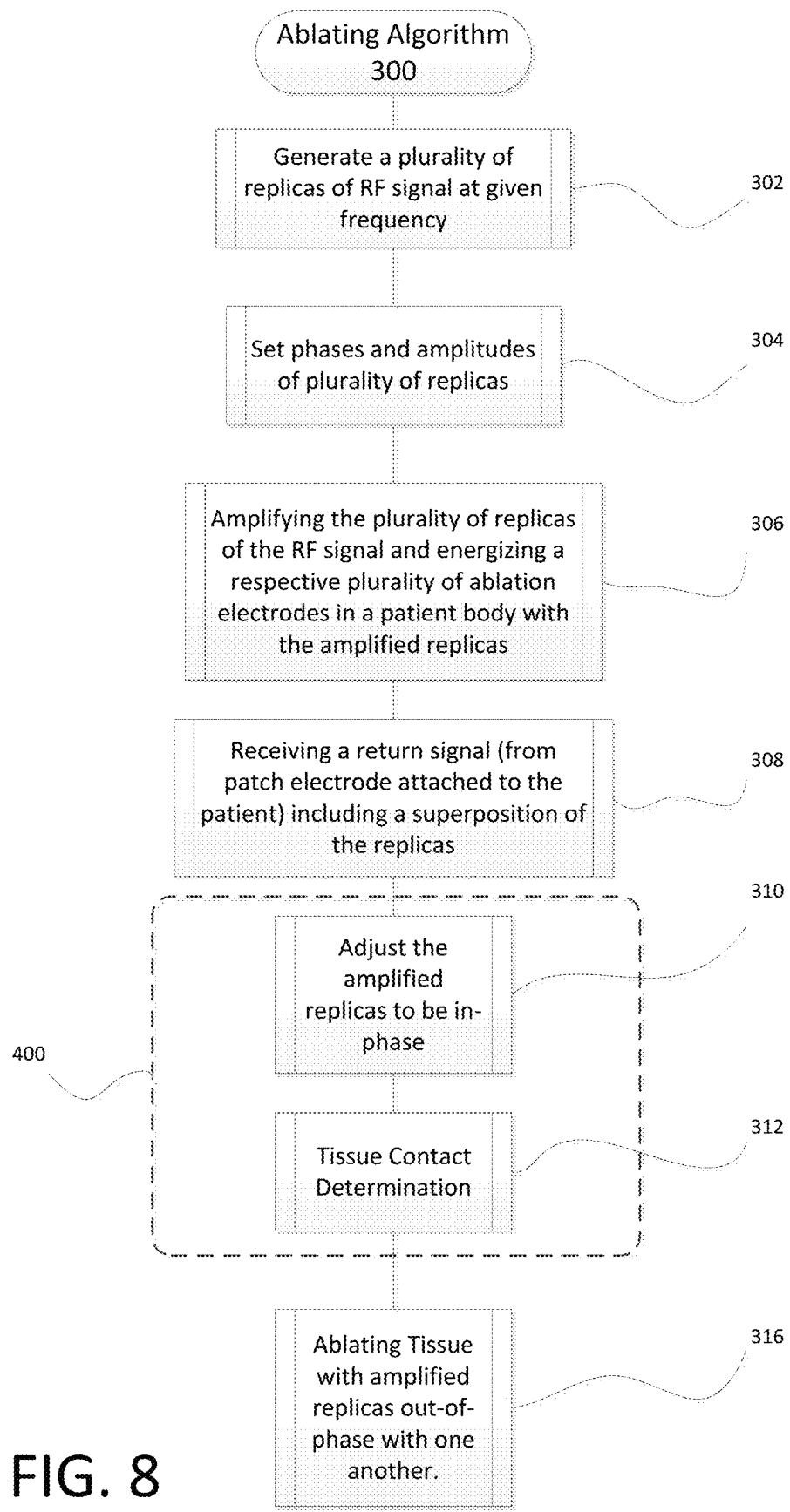
FIG. 8 and FIG. 9 show a flowchart of steps of an ablation algorithm in accordance with an embodiment of the inventions.

In FIG. 8, algorithm 300 starts with the system 134 programmed to generate a plurality of replicas of an RF signal at a given frequency in step 302. At step 304, the phases and amplitudes of the replicas for the n-ablation electrodes are set. At step 306, the system is programmed to amplify the plurality of replicas and energizes or drives a respective plurality of n ablation electrodes in a patient body with the amplified replicas. At step 308, the system 134 is programmed to receive a return signal from a patch electrode 262 that may include a superposition of the replicas. At step 310, the system 134 is programmed to adjust the replicas of the current injected to the n-ablation electrodes to be in-phase. At step 312, the system 134 is programmed to determine whether tissue is in contact with the electrode(s). Steps 310 and 312 are further described as subroutine 400 in FIG. 9.

Figure 9:
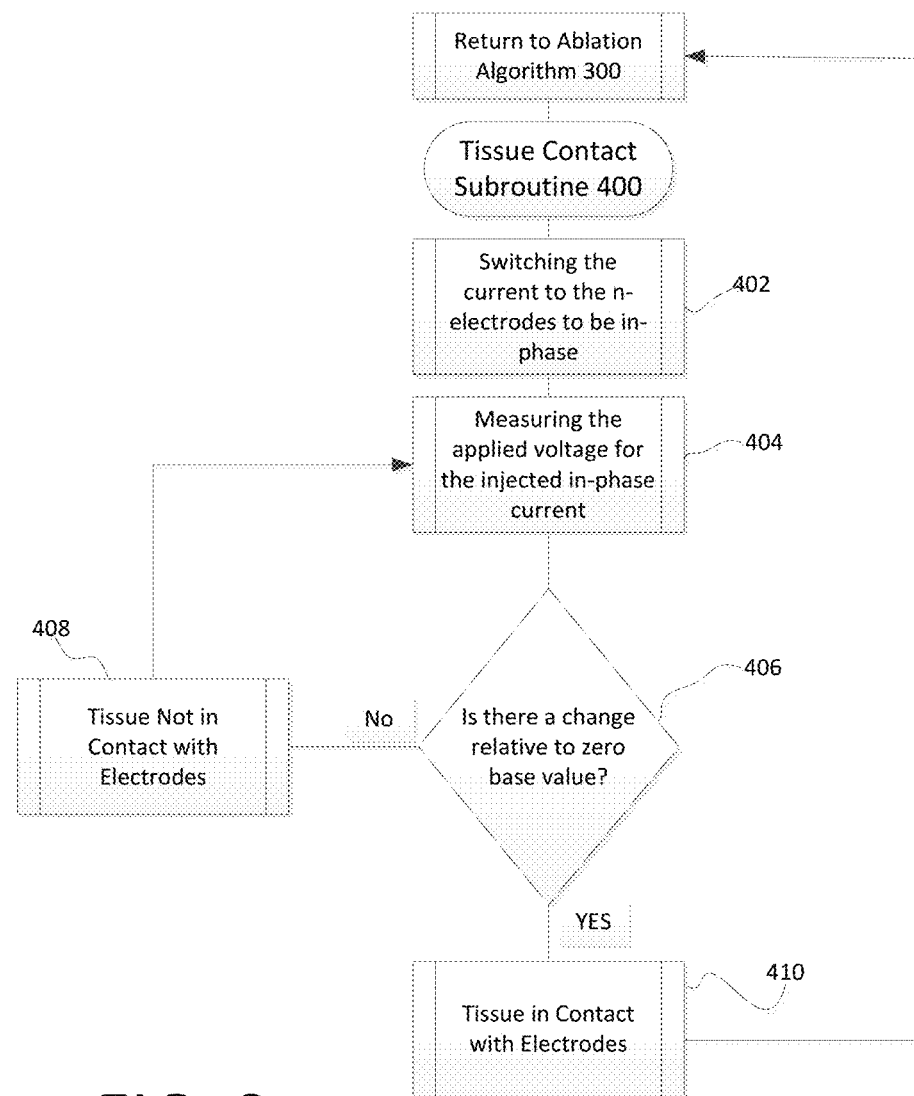

With reference to FIG. 9, details of the tissue contact determination can be understood by one skilled in the art to generate suitable computer codes. In general, contact with tissue can be detected when the in-phase current injected into each electrode 279 requires a voltage (as measured by voltage and current sensors 256) increase of approximately 3-10% or more over the typical ablation voltage (for a given amount of tissue impedance) needed in the ablation mode. Hence, we have devised a technique that allows for the checking of sufficient tissue-contact during an ablation procedure by switching, at step 402, the current or replicas injected to the n electrodes 279 to be in-phase while applying a voltage at increasing level and at step 404, measuring the voltage and current with analyzer 260. At step 406, if there is no change in the form of zero base value then the system algorithm returns a "no" and determines that the electrode as not in sufficient contact with body tissues. The system can flag the electrode(s) as not being in contact at step 408 before returning to step 404. On the other hand, once tissue contact is confirmed (i.e., when the in-phase current being injected [i.e., of the replicas] requires a change relative to the zero base value) from the system returning a "yes" in step 406, the controller can flag the electrode(s) as being in contact in step 410. Thereafter, the subroutine 400 returns to the ablation algorithm 300 (FIG. 8) to switch or change the n electrodes at step 316 to be out of-phase so as to continue ablation of the tissue (which tissue is now in sufficient contact with the electrode(s)). It is intended that such operation (steps 402, 404 and 406) between contact checking (i.e., switching to in-phase electrodes 279) and tissue ablating of step 316 (FIG. 8, changing to out-of-phase electrodes 279) would occur at a very rapid rate of many times per second, typically switching at approximately 50 Hz. The number of n electrodes can be any number from about 2 to about 192.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A radio frequency (RF) ablation system, comprising:
a signal generator configured to generate an RF signal having a given frequency;
control circuitry, configured to set phases and amplitudes of a plurality of replicas of the RF signal generated by the signal generator;
a plurality of non-linear amplifiers, configured to amplify the plurality of replicas of the RF signal, and to drive a respective plurality of ablation electrodes in a patient body with the amplified replicas; and
a processor configured to:
analyze a return signal from a patch electrode attached to the patient body, the return signal comprising a superposition of the plurality of replicas sensed by the patch electrode,
ablate the target tissue with the plurality of ablation electrodes in an ablation mode, and
adaptively adjust phases and amplitudes of the amplified replicas, based at least in part on the return current, by controlling the control circuitry such that in the ablation mode of operation the amplified replicas are adjusted such that the phases of the amplified replicas differ from one another and crosstalk between the electrodes of the plurality of electrodes is reduced.

2. The system according to claim 1, wherein in the ablation mode of operation the phases of the amplified replicas differ from one another by at least 3.6 degrees.

3. The system according to claim 1, further comprising a measurement circuit, configured to measure the replicas that are amplified respectively by the amplifiers, wherein the processor is configured to adjust the phases and the amplitudes of the replicas based on the measured replicas in the ablation mode of operation.

4. The system according to claim 1, and comprising a catheter, configured to be inserted into the patient body, to which the plurality of electrodes are attached.

5. The system according to claim 4, wherein the catheter comprises one of an inflatable balloon and an expandable basket assembly.

6. The system of claim 1, wherein the processor is further configured to:
determine, based at least in part on the return signal while the plurality of replicas are in phase with each other, that a state of contact exists between the ablation electrodes and target tissue in a tissue contact mode.

7. The system according to claim 1, wherein in the ablation mode of operation a voltage of the RF signal is between 27V RMS and 47VRMS.

8. The system according to claim 6, wherein a tissue contacted in the tissue contact mode comprises a pulmonary vein.

9. The system of claim 1,
wherein the return signal comprises a return current, and
wherein the processor is configured to adaptively adjust phases and amplitudes of the amplified replicas based at least in part on the return current.

10. A method of ablation, comprising the steps of:
generating a plurality of replicas of an RF signal having a given frequency;
setting phases and amplitudes of the plurality of replicas;
amplifying the plurality of replicas of the RF signal, and driving a respective plurality of ablation electrodes in a patient body with the amplified replicas;
analyzing a return signal comprising a superposition of the plurality of replicas sensed by a patch electrode;
determining, based at least in part on the return signal while the plurality of replicas are in phase with each other, that a state of contact exists between the ablation electrodes and target tissue in the patient in a tissue contact mode;
ablating the target tissue with the ablation electrodes in an ablation mode of operation; and
adjusting, during the ablation mode, phases of the plurality of replicas to be out of phase with each other and reduce cross talk between electrodes of the respective plurality of ablation electrodes.

11. The method according to claim 10, wherein in the ablation mode of operation the phases of the amplified replicas differ from one another by at least 3.6 degrees.

12. The method according to claim 10, further comprising:
making measurements of the replicas; and
responsively to the measurements zeroing crosstalk currents between the ablation electrodes by adjusting the phases and the amplitudes of the replicas in the ablation mode of operation.

13. The method of claim 10, wherein the determining step comprises:
switching the replicas of current injected to the plurality of ablation electrodes to be in-phase while applying a voltage at increasing level and measuring the replicas of current with an analyzer; and
checking whether tissue is in contact when the in-phase replicas of current injected into each electrode requires a voltage increase greater than a zero base value.

14. The method according to claim 10, and comprising attaching the plurality of electrodes to a catheter configured to be inserted into the patient body.

15. The method according to claim 10, wherein a tissue contacted in the tissue contact mode comprises a pulmonary vein.

16. The method according to claim 10, wherein in the ablation mode of operation a voltage of the RF signal is between 27V RMS and 47VRMS.

17. A method to ablate tissue in a system having a signal generator configured to generate an RF signal coupled to a control circuitry, the control circuitry configured to set phases and amplitudes of a plurality of replicas of the RF signal generated by the signal generator with a plurality of non-linear amplifiers to amplify the plurality of replicas of the RF signal and drive a respective plurality of n ablation electrodes in a patient body with the amplified replicas; and a processor, configured to analyze a return signal comprising a superposition of the plurality of replicas sensed by a patch electrode attached to the patient body, the method comprising the steps of: switching the replicas of current injected to the n ablation electrodes to be in-phase while applying a voltage at increasing level and measuring the replicas of current with an analyzer, checking whether tissue is in contact when the in-phase replicas of current injected into each electrode requires a change in voltage greater than a zero base value, and changing the n ablation electrodes to be out of-phase to continue ablation of the tissue such that phases of the plurality of replicas are adjusted to be out of phase with each other and cross-talk between electrodes of the n ablation electrodes is reduced.

18. The method of claim 17, wherein the steps of switching the n ablation electrodes to be in-phase and changing the n ablation electrodes to be out-of-phase are conducted at a rate many times per second.

19. The method of claim 18, wherein the rate comprises a rate of 50 Hz.

20. The method of claim 17, wherein the n ablation electrodes comprise any number of electrodes from 2 to 192.

* * * * *